United States Patent [19]

Nishio et al.

[11] Patent Number: 4,956,374
[45] Date of Patent: Sep. 11, 1990

[54] POLYSUBSTITUTED THIAZOLYLPYRIDINE CARBOXYAMIDE ANTIFUNGAL ANTIBIOTIC

[75] Inventors: Maki Nishio, Tokyo; Shigeyuki Ando, Mitaka; Takeo Miyaki, Yokohama; Masataka Konishi, Kawasaki; Toshikazu Oki, Yokohama, all of Japan

[73] Assignee: Bristol-Myers Company, New York, N.Y.

[21] Appl. No.: 226,016

[22] Filed: Jul. 29, 1988

[51] Int. Cl.$^5$ ............... C07D 417/04; A01N 43/78
[52] U.S. Cl. ............................. 514/342; 546/256; 546/280; 424/114
[58] Field of Search ............... 514/342; 546/280, 256

[56] References Cited

U.S. PATENT DOCUMENTS

| | | | |
|---|---|---|---|
| 4,798,838 | 1/1989 | Kojima et al. | 514/342 |
| 4,849,434 | 7/1989 | Enomoto et al. | 514/342 |
| 4,898,947 | 2/1990 | Meguro et al. | 546/280 |

*Primary Examiner*—Alan L. Rotman
*Attorney, Agent, or Firm*—Robert E. Carnahan

[57] ABSTRACT

Novel antifungal antibiotic compounds have the structural formula

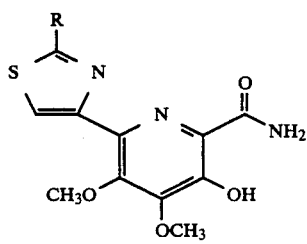

A preferred compound where R is 4-hydroxypentyl is denoted BU-3557B$_2$. A complex of said compounds is produced by fermenting a culture of *Sacchrothrix aerocolonigenes* strain N806-4 (ATCC 53712). The complex is recovered by adsorption on nonionic porous polymer resin adsorbent and individual component compounds exhibit in vitro activity against fungi and Gram-positive bacteria and BU-3557B$_2$ demonstrates in vitro antiprotazoal activity. BU-3557B$_2$ demonstrates in vivo activity against *C. albicans* vaginal infection and BU-3557A$_3$ (where R is 1,5-dihydroxy-5,5-dimethylpentyl) demonstrates in vivo activity against *C. albicans* systemic infection.

8 Claims, 8 Drawing Sheets

POLYSUBSTITUTED THIAZOLYLPYRIDINE CARBOXYAMIDE ANTIFUNGAL ANTIBIOTIC

FIELD OF THE INVENTION

This invention relates to novel antifungal antibiotic compounds, their production, and their use in treating fungal infections. This invention also relates to a novel culture for use in producing antifungal antibiotic.

BACKGROUND OF THE INVENTION

There are relatively few known effective antifungal antibiotics. Because of this, there has been a continuing search to uncover microorganisms for screening for production of antifungal fermentation products. The present invention is the result of this effort.

SUMMARY OF THE INVENTION

The novel antifungal antibiotic compounds herein have the following structural formula:

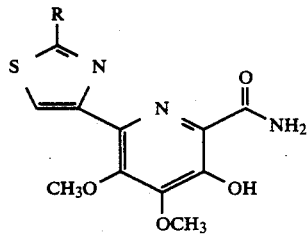

wherein R is pentyl having one or more substituents at one or more positions selected from the group consisting of lower alkyl (i.e. $C_1$–$C_3$ alkyl), hydroxy and oxo.

A preferred compound is denoted BU-3557B$_2$ and has the above structural formula where R is 4-hydroxypentyl.

A complex of said compounds is produced by fermenting a culture of a newly uncovered strain of Saccharothrix designated Saccharothrix aerocolonigenes strain N806-4 (ATCC 53712). The production method involves cultivating said strain under aerobic conditions in an aqueous nutrient medium containing assimilable sources of carbon and nitrogen until a substantial amount of said complex is produced and recovering said complex. Individual compounds can be recovered from said complex by chromatography.

A pharmaceutical composition for treatment of antifungal infectious comprises and effective antifungal amount of compound as described above in combination with pharmaceutical carrier of diluent.

An animal host affected by a fungal infection sensitive to compound of the present invention is therapeutically treated by administering to said host an effective antifungal dose of said compound in the form of said pharmaceutical composition. In the therapeutic treatment of Candida albicans systemic infection, administration of compound of the present invention is readily carried out by topical application.

DETAILED DESCRIPTION

Figure 1:
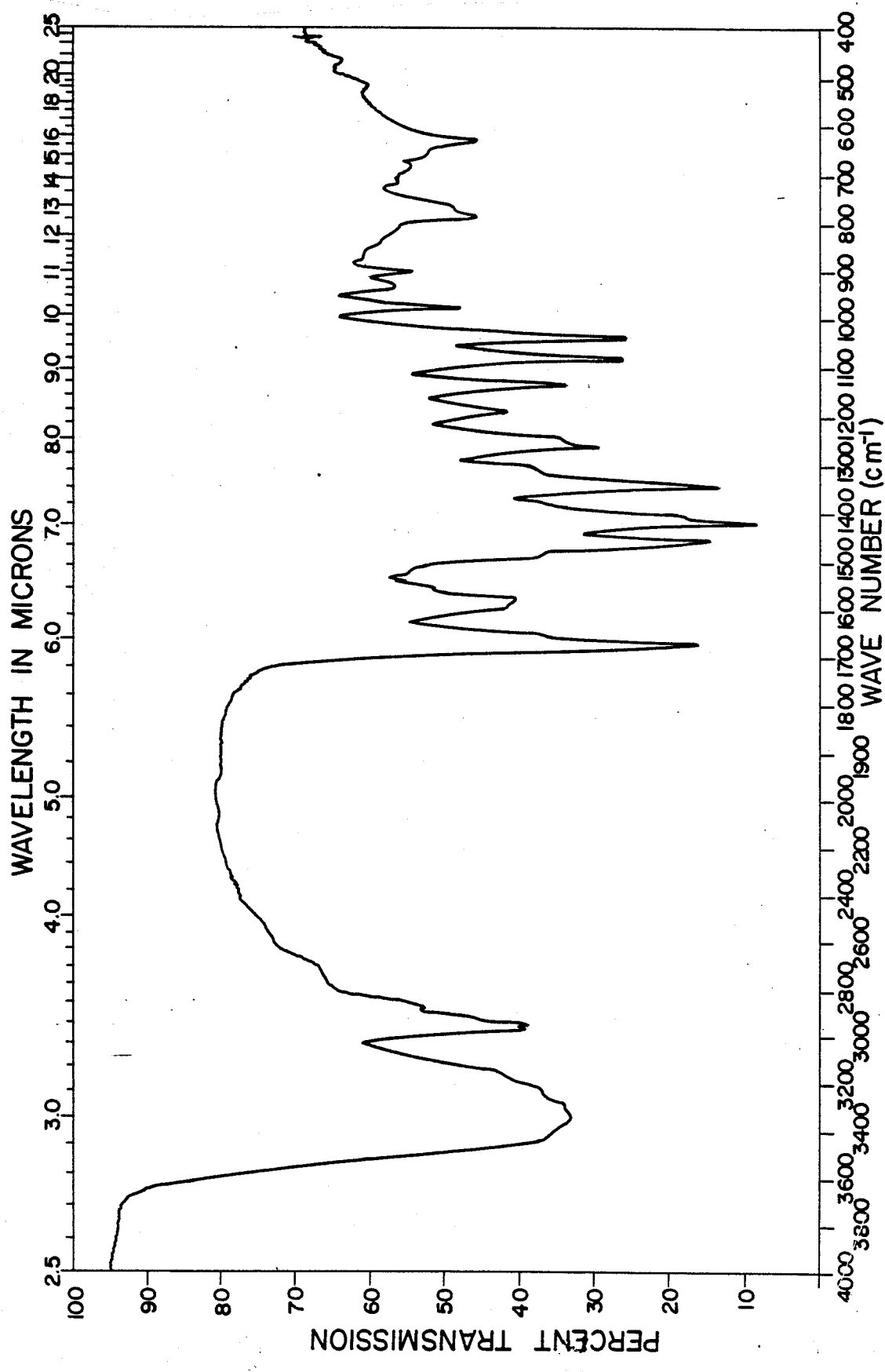
FIG. 1 depicts the infrared spectrum of BU-3557 A$_3$, i.e., compound of the above structural formula where R is 1,5-dihydroxy-5,5-dimethylpentyl.

In the novel compounds herein the substituents on the pentyl of R typically are 1 to 4 in number and occur at 1 or positions especially at the 1-position, 3-position, 4-position and/or 5-position and are selected from the group consisting of methyl, hydroxy and oxo. In 7 compounds that have been prepared R contains an oxo substituent or a hydroxy substituent at the 4-position of its pentyl.

Specific compounds that have been prepared and identified include those with the above structural formula where R is 1,4-dihydroxypentyl (designated BU-3557A$_1$), where R is 1,4-dihydroxy-4-methylpentyl (designated BU-3557A$_2$), where R is 1,5-dihydroxy-5,5-dimethylpentyl (designated BU-3557A$_3$), where R is 4-oxopentyl (designated BU-3557B$_1$), where R is 4-hydroxypentyl (designated BU-3557B$_2$), where R is 4-hydroxy-4-methylpentyl (designated BU-3557B$_3$), where R is a 3-hydroxypentyl (designated BU-3557C$_1$), where R is 4-methyl-5-hydroxypentyl (designated BU-3557C$_2$), where R is 3-methyl-4-hydroxypentyl (designated BU-3557C$_3$), where R is 3-methyl-4-oxopentyl (designated BU-3557C$_4$), where R is 1-hydroxypentyl (designated BU-3557C$_5$), and where R is 5-hydroxy-5,5-dimethylpentyl (designated BU-3557D). BU-3557B$_2$ is the preferred compound herein in that it has been found to be relatively active. BU-3557B$_2$ has been determined by x-ray diffraction to be 6-[2-(4-hydroxypentyl)-thiazol4-yl]-3-hydroxy-4,5-dimethoxypyridine-2-carboxamide.

Physico-chemical properties for each of the specific compounds referred to above are set forth in Table I below:

TABLE I

| | BU-3557A$_1$ | BU-3557A$_2$ | BU-3557A$_3$ | BU-3557B$_1$ |
|---|---|---|---|---|
| Nature | White powder | White powder | White powder | White crystalline powder |
| M.p. | 56.5–58.5° C. | 60–63° C. | 69–72° C. | 151–153° C. |
| $[\alpha]_D^{25}$ | −11°(c = 0.5, CHCl$_3$) | −14°(c = 0.5, CHCl$_3$) | −19°(c = 0.25, CHCl$_3$) | 0°(c = 0.5, CHCl$_3$) |
| UV $\lambda_{max}$ ($\epsilon$) nm | | | | |
| in MeOH | 219(25,000) | 219(25,500) | 218(26,400) | 219(25,900) |
| | 242(22,700) | 242(23,500) | 242(23,700) | 242(23,600) |
| | 315(6,700) | 316(6,800) | 317(6,800) | 316(6,900) |

TABLE I-continued

|  | | | | |
|---|---|---|---|---|
| in 0.1N HCl—MeOH (1:9) | 220(25,700) 243(25,700) 318(7,500) | 220(23,900) 243(23,900) 318(6,900) | 220(25,000) 243(25,100) 317(7,300) | 220(23,900,sh) 243(26,400) 318(8,000) |
| in 0.1N NaOH—MeOH (1:9) | 220(23,400) 251(21,600) 281(17,200) 342(9,000) | 220(23,600) 251(21,500) 282(17,000) 342(9,000) | 220(24,200) 251(22,200) 282(17,400) 342(9,200) | 220(23,300) 251(23,300) 292(16,600) 341(9,100) |
| IR $\nu_{max}^{KBr}$ cm$^{-1}$ | 3400,1665,1590 | 3300,1665,1580 | 3350,1665,1580 | 3385,1705,1665,1600 |
| MS (EI) m/z | 383(M$^+$),368,338 | 397(M$^+$),382,364,323 | 411(M$^+$),396,393,378 | 365(M$^+$),295,219 |
| Molecular formula | $C_{16}H_{21}N_3SO_6$ | $C_{17}H_{23}N_3SO_6$ | $C_{18}H_{25}N_3SO_6$ | $C_{16}H_{19}N_3SO_5$ |

|  | BU-3557B$_2$ | BU-3557B$_3$ | BU-3557C$_1$ | BU-3557C$_2$ |
|---|---|---|---|---|
| Nature | White crystalline powder | White crystalline powder | White crystalline powder | White crystalline powder |
| M.p. | 171–172.5° C. | 187.5–189.5° C. | 152.5–154° C. | 130.5–133° C. |
| $[\alpha]_D^{25}$ | 0°(c = 0.5, CHCl$_3$) | 0°(c = 0.5, CHCl$_3$) | +14°(c = 0.25, CHCl$_3$) | −8°(c = 0.25, CHCl$_3$) |
| UV $\lambda_{max}$ ($\epsilon$) nm | | | | |
| in MeOH | 219(26,100) 242(23,500) 317(6,800) | 220(25,400) 242(23,200) 317(6,800) | 220(25,000) 243(22,200) 317(6,600) | 220(26,000) 243(24,000) 318(7,100) |
| in 0.1N HCl—MeOH (1:9) | 220(23,500,sh) 243(26,900) 318(8,100) | 220(22,100,sh) 243(26,500) 318(7,900) | 222(23,100,sh) 242(23,500) 317(7,500) | 222(22,500,sh) 243(26,600) 318(8,200) |
| in 0.1N NaOH—MeOH (1:9) | 221(23,300) 252(21,100) 293(16,600) 342(9,000) | 218(21,400) 252(20,200) 294(16,200) 342(8,700) | 220(22,100) 252(19,800) 294(15,700) 342(8,400) | 217(22,100) 253(20,600) 294(16,800) 342(9,100) |
| IR $\nu_{max}^{KBr}$ cm$^{-1}$ | 3300,1675,1600 | 3240,1680,1610 | 3300,1670,1600 | 3200,1670,1600 |
| MS (EI) m/z | 367(M$^+$),352,335 | 381(M$^+$),366,332 | 367(M$^+$),352,338 | 381(M$^+$),366,295 |
| Molecular formula | $C_{16}H_{21}N_3SO_5$ | $C_{17}H_{23}N_3SO_5$ | $C_{16}H_{21}N_3SO_5$ | $C_{17}H_{23}N_3SO_5$ |

|  | BU-3557C$_3$ | BU-3557C$_4$ | BU-3557C$_5$ | BU-3557D |
|---|---|---|---|---|
| Nature | White crystalline powder | White crystalline powder | White crystalline powder | White crystalline powder |
| M.p. | 165.5–167.5° C. | 124.5–126.5° C. | 138–140° C. | 146.5–148° C. |
| $[\alpha]_D^{25}$ | +20°(c = 1.0, CHCl$_3$) | 0°(c = 1.0, CHCl$_3$) | +19°(c = 1.0, CHCl$_3$) | 0°(c = 1.0, CHCl$_3$) |
| UV $\lambda_{max}$ ($\epsilon$) nm | | | | |
| in MeOH | 220(25,800) 242(23,200) 317(6,800) | 220(25,900) 243(23,900) 317(7,100) | 220(25,700) 243(23,900) 317(7,100) | 219(26,300) 242(23,500) 317(6,800) |
| in 0.1N HCl—MeOH (1:9) | 222(25,000,sh) 244(28,300) 318(8,400) | 223(23,200,sh) 243(26,100) 318(8,000) | 220(24,600) 243(24,700) 317(7,400) | 220(23,300,sh) 243(26,400) 317(8,000) |
| in 0.1N NaOH—MeOH (1:9) | 220(17,300) 251(21,000) 294(16,600) 341(8,800) | 217(22,300) 252(20,600) 294(16,700) 342(9,100) | 217(22,200) 252(20,700) 283(16,700) 343(8,900) | 221(22,900) 252(20,800) 292(16,400) 342(8,800) |
| IR $\nu_{max}^{KBr}$ cm$^{-1}$ | 3200,1670,1605 | 3390,1705,1660,1590 | 3300,1670,1600 | 3250,1675,1610 |
| MS (EI) m/z | 381(M$^+$),366,336 | 379(M$^+$),364,308 | 367(M$^+$),352,311 | 395(M$^+$),380,362 |
| Molecular formula | $C_{17}H_{23}N_3SO_5$ | $C_{17}H_{21}N_3SO_5$ | $C_{16}H_{21}N_3SO_5$ | $C_{18}H_{25}N_3SO_5$ |

Analysis of $^1$H-NMR spectra for each of the compounds specifically mentioned above at (400 MHz, in CDCl$_3$) is set forth in Table II below.

TABLE II

|  | BU-3557A$_1$ | BU-3557A$_2$ | BU-3557A$_3$ | BU-3557B$_1$ | BU-3557B$_2$ | BU-3557B$_3$ |
|---|---|---|---|---|---|---|
| Side chain ® | | | | | | |
| C-1 | 5.17(1H,t) | 5.33(1H,t) | 5.38(1H,t) | 3.14(2H,t) | 3.00(1H,m) 3.25(1H,m) | 3.06(2H,t) |
| 2 | 2.12(2H,m) | 2.13(1H,m) 2.24(1H,m) | 2.04(2H,m) | 2.12(2H,qui) | 2.00(1H,m) 2.20(1H,m) | 2.00(2H,qui) |
| 3 | 1.68(2H,m) | 1.78(2H,m) | 1.61(4H,m) | 2.59(2H,t) | 1.64(2H,m) | 1.65(2H,t) |
| 4 | 3.90(1H,m) | | | | 3.94(1H,m) | |
| 5 | 1.22(3H,t) | 1.26(3H,s) | | 2.15(3H,s) | 1.18(3H,d) | 1.13(3H,s) |
| 6 | | 1.26(3H,s) | 1.19(3H,s) | | | 1.13(3H,s) |
| 7 | | | 1.22(3H,s) | | | |
| Aromatic nucleus | | | | | | |
| —OCH$_3$ | 3.95(3H,s) 4.06(3H,s) | 4.01(3H,s) 4.11(3H,s) | 4.00(3H,s) 4.11(3H,s) | 3.96(3H,s) 4.12(3H,s) | 3.97(3H,s) 4.09(3H,s) | 3.89(3H,s) 3.94(3H,s) |
| Aromatic —H | 7.88(1H,s) | 7.98(1H,s) | 7.98(1H,s) | 7.81(1H,s) | 7.90(1H,s) | 7.83(1H,s) |
| —NH or | 5.80(1H,br) | 5.70(1H,br) | 5.76(1H,br) | 5.84(1H,br) | 5.62(1H,br) | 5.53(1H,br) |
| —OH | 9.15(1H,br) 12.65(1H,s) | 9.32(1H,br) 12.88(1H,s) | 9.40(1H,br) 12.93(1H,s) | 8.43(1H,br) 12.49(1H,s) | 6.88(1H,br) 9.78(1H,br) 12.91(1H,s) | 5.70(1H,br) 9.69(1H,br) 12.81(1H,s) |

|  | BU-3557C$_1$ | BU-3557C$_2$ | BU-3557C$_3$ | BU-3557C$_4$ | BU-3557C$_5$ | BU-3557D |
|---|---|---|---|---|---|---|
| Side chain ® | | | | | | |

TABLE II-continued

| | | | | | | |
|---|---|---|---|---|---|---|
| C-1 | 3.25(2H,m) | 3.25(2H,t) | 3.15(2H,t) | 3.07(2H,t) | 5.22(1H,t) | 3.20(2H,t) |
| 2 | 2.05(2H,m) | | 2.13(2H,m) | 1.86(1H,m) 2.24(1H,m) | 1.95(2H,m) | 1.90(2H,tt) |
| 3 | 3.75(1H,m) | 1.3–2.1 (5H,m) | 1.70(1H,m) 3.55(1H,m) | 2.65(1H,qt) | 1.2–1.6 (4H,m) | 1.57(4H,m) |
| 4 | 1.52(2H,m) | | | | | |
| 5 | 0.98(3H,t) | 3.55(2H,t) | 1.18(3H,d) | 2.16(3H,s) | 0.94(3H,t) | |
| 6 | | 0.92(3H,d) | 0.95(3H,d) | 1.17(3H,d) | | 1.19(3H,s) |
| 7 | | | | | | 1.19(3H,s) |
| Aromatic nucleus | | | | | | |
| —OCH₃ | 4.00(3H,s) | 3.96(3H,s) | 3.98(3H,s) | 3.94(3H,s) | 3.92(3H,s) | 3.97(3H,s) |
| | 4.10(3H,s) | 4.10(3H,s) | 4.08(3H,s) | 4.11(3H,s) | 4.10(3H,s) | 4.11(3H,s) |
| aromatic —H | 7.80(1H,s) | 7.92(1H,s) | 7.90(1H,s) | 7.77(1H,s) | | 7.90(1H,s) |
| —NH or | 5.58(1H,br) | 5.60(1H,br) | 5.55(1H,br) | 5.89(1H,br) | 5.95(1H,br) | 5.65(1H,br) |
| —OH | 8.98(1H,br) | 9.70(1H,br) | 9.85(1H,br) | 8.25(1H,br) | 6.70(1H,br) | 9.39(1H,br) |
| | 12.65(1H,s) | 12.90(1H,s) | 12.90(1H,s) | 12.41(1H,s) | 9.30(1H,br) 12.97(1H,s) | 12.78(1H,s) |

Figure 2:
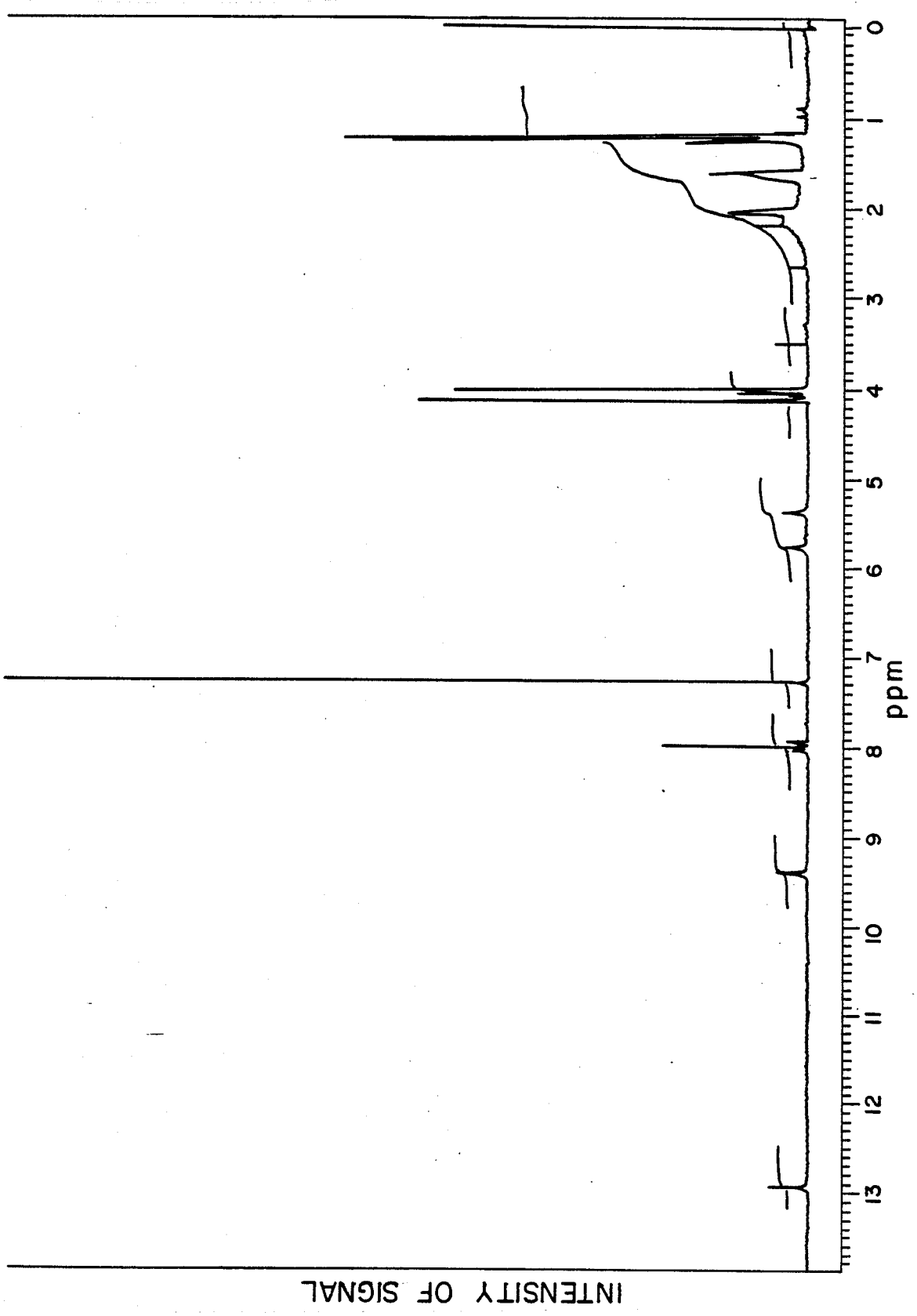
FIG. 2 depicts the $^1$H-NMR spectrum of BU-3557 A$_3$ at 400 MHz, in CDCl$_3$.
Figure 4:
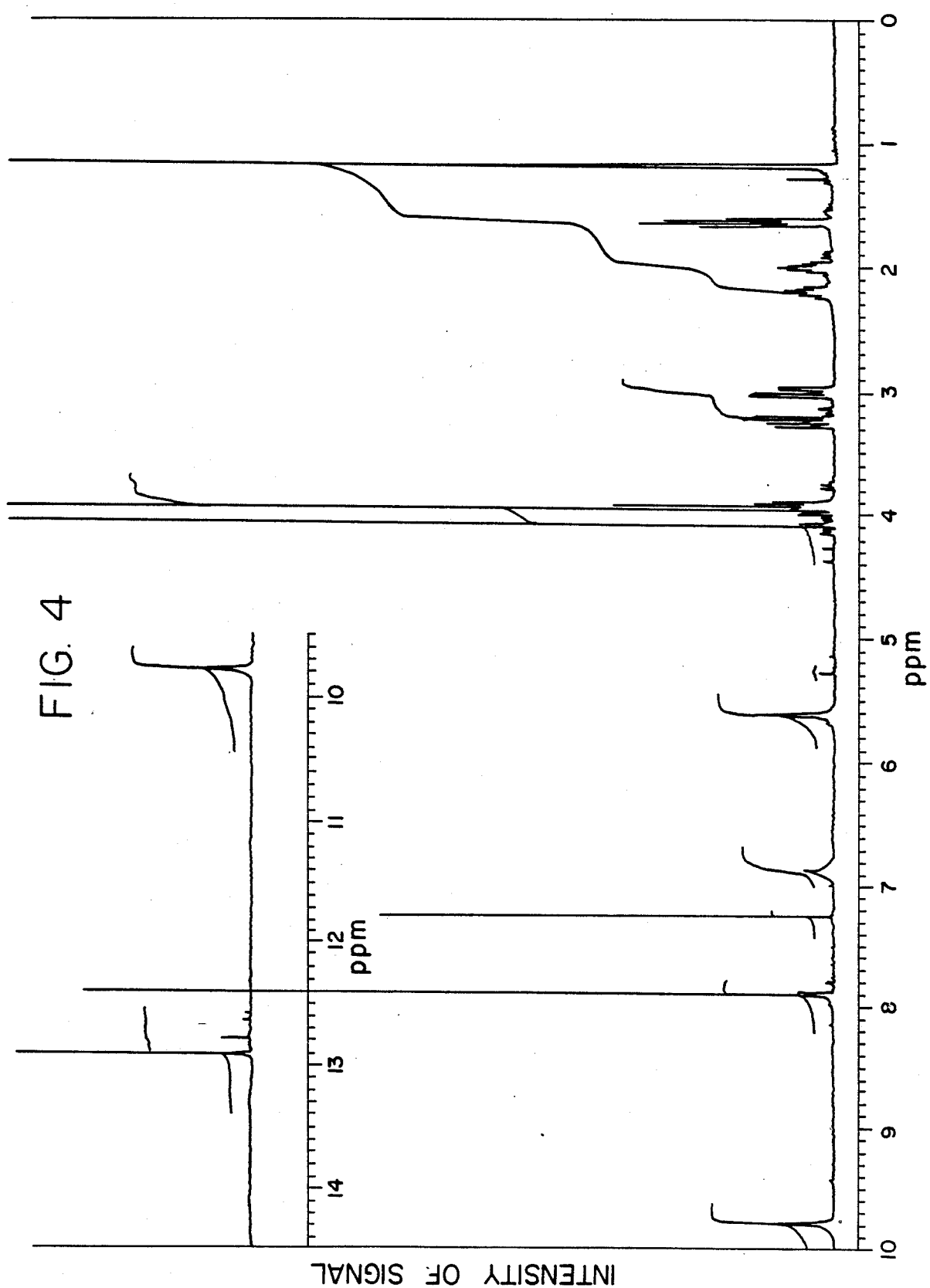
FIG. 4 depicts the $^1$H-NMR spectrum of BU-3557B$_2$ at 400 MHz in CDCl$_3$.
Figure 6:
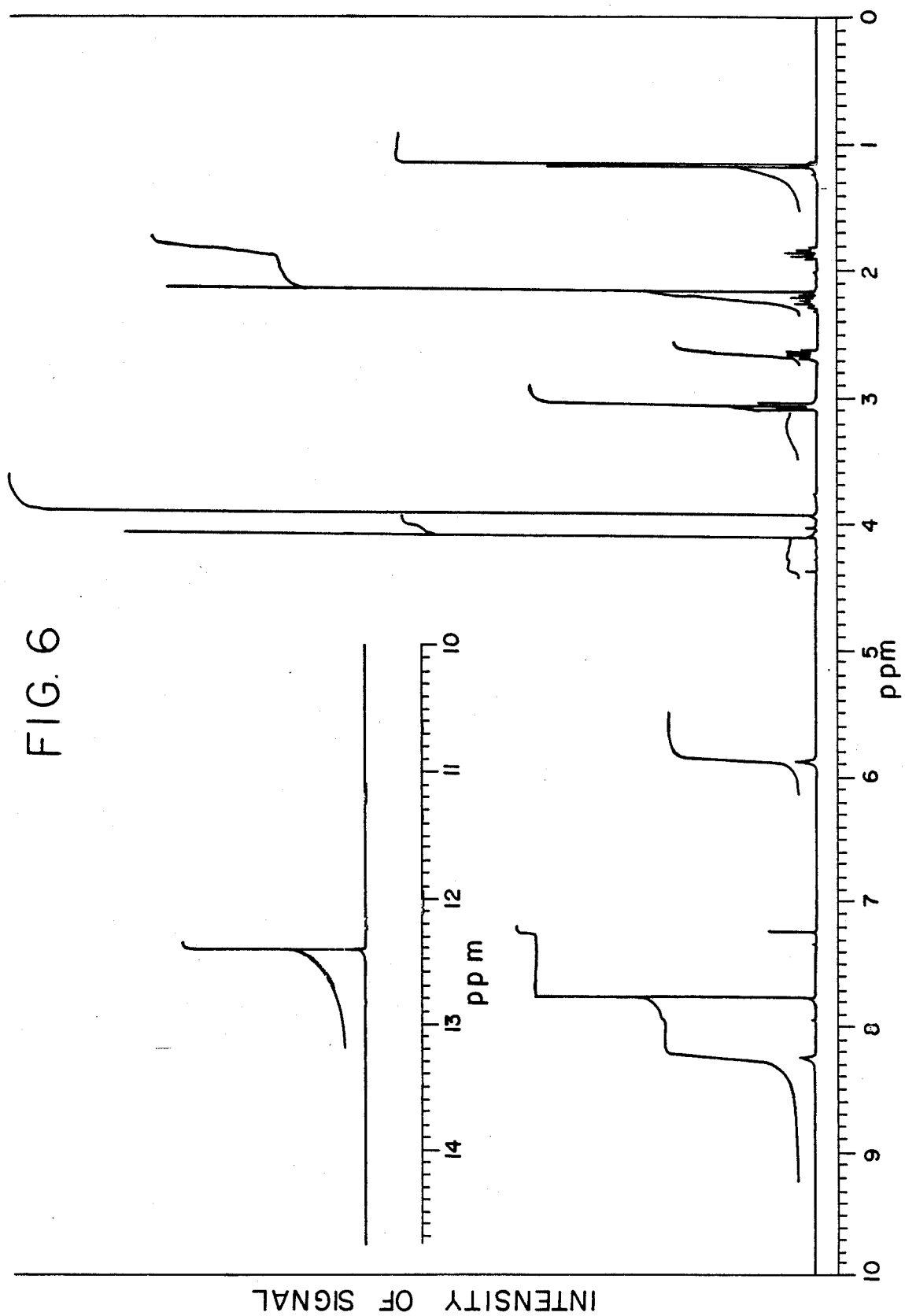
FIG. 6 depicts the $^1$H-NMR spectrum of BU-3557C$_4$ at 400 MHz in CDCl$_3$.
Figure 8:
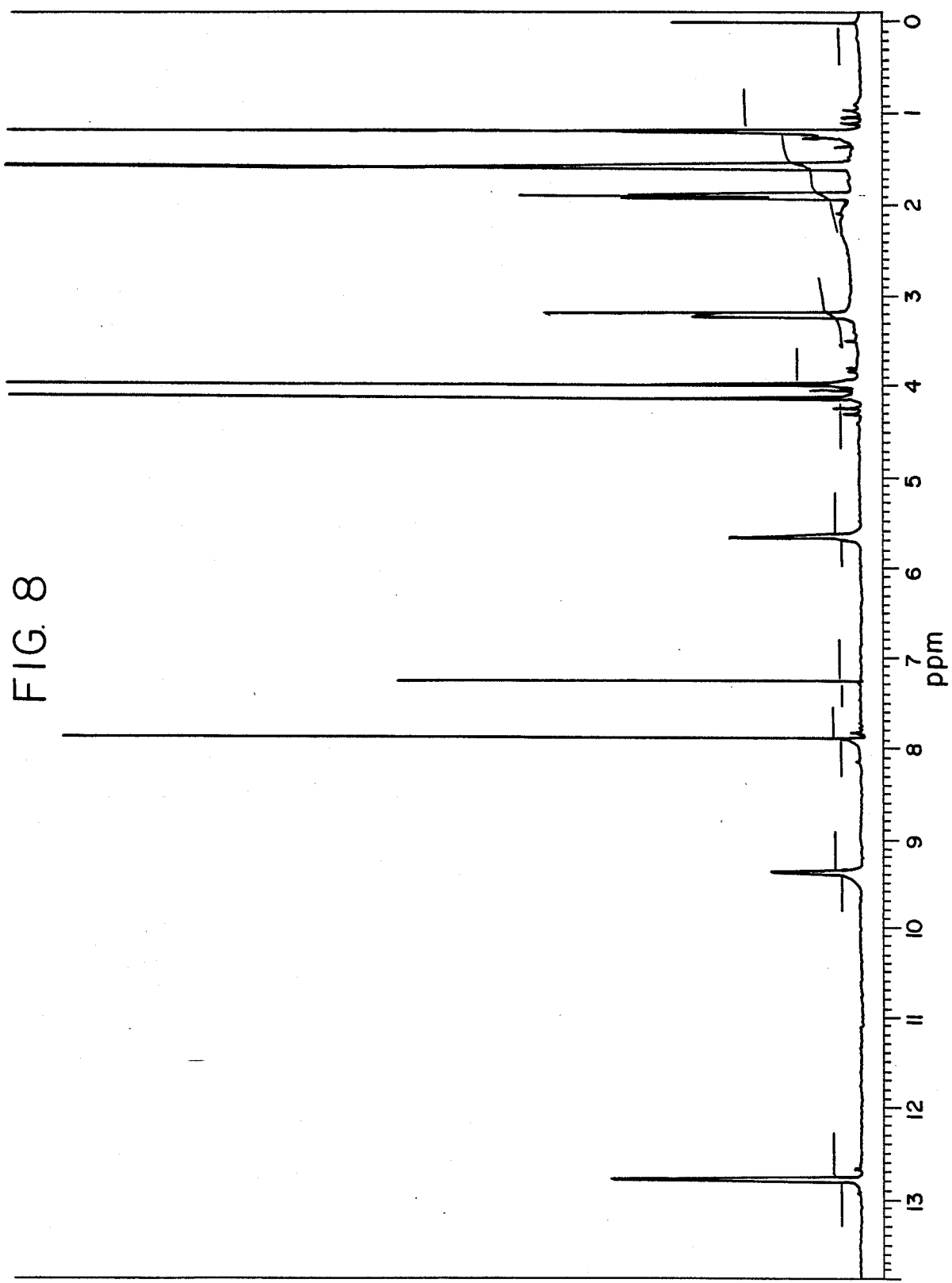
FIG. 8 depicts the $^1$H-NMR spectrum of BU-3557D at 400 MHz in CDCl$_3$.

The $^1$H-NMR spectra for BU-3557A₃, BU-3557B₂, BU-3557C₄ and BU-3557D are respectively presented in FIGS. 2, 4, 6 and 8.

Analysis of the $^{13}$C-NMR spectra for compounds BU-3557A₃, BU-3557B₁, BU-3557B₂, BU-3557B₃, BU-3557C₃, BU-3557C₄ and BU-3557D is set forth in Table III below.

TABLE III

| | BU-3557A₃ | BU-3557B₁ | BU-3557B₂ | BU-3557B₃ | BU-3557C₃ | BU-3557C₄ | BU-3557D |
|---|---|---|---|---|---|---|---|
| Side chain ® | | | | | | | |
| C-1 | 71.31 d | 32.33 t | 31.70 t | 32.54 t | 30.06 t | 32.75 t | 32.13 t |
| 2 | 38.16 t | 23.86 t | 22.44 t | 21.07 t | 28.11 t | 30.84 t | 29.30 t |
| 3 | 19.76 t | 42.40 t | 38.98 t | 41.34 t | 40.89 d | 46.18 d | 22.36 t |
| 4 | 42.55 t | 208.03 s | 65.19 d | 70.53 s | 70.35 d | 212.01 s | 41.75 t |
| 5 | 71.14 s | 30.05 q | 23.30 q | 29.71 q | 21.22 q | 28.40 q | 70.94 s |
| 6 | 29.02 q | | | 29.71 q | 16.81 q | 16.71 q | 29.30 q |
| 7 | 29.61 q | | | | | | 29.30 q |
| Aromatic nucleus | | | | | | | |
| —OCH₃ | 60.79 q | 60.83 q | 60.72 q | 60.74 q | 60.67 q | 60.79 q | 60.74 q |
| | 60.85 q | 61.07 q | 60.75 q | 60.74 q | 60.71 q | 60.87 q | 60.87 q |
| aromatic | 119.40 d | 118.54 d | 118.44 d | 118.55 d | 118.36 d | 118.61 d | 118.57 d |
| carbon | 127.38 s | 127.12 s | 127.59 s | 127.58 s | 127.66 s | 127.31 s | 127.37 s |
| and | 136.87 s | 137.43 s | 136.68 s | 136.96 s | 136.64 s | 137.19 s | 137.53 s |
| amide | 147.74 s | 147.88 s | 147.66 s | 147.71 s | 147.66 s | 147.73 s | 147.79 s |
| carbon | 149.89 s | 150.26 s | 149.86 s | 149.94 s | 149.87 s | 150.39 s | 150.40 s |
| | 150.47 s | 150.59 s | 150.27 s | 150.36 s | 150.27 s | 150.47 s | 150.50 s |
| | 152.97 s | 152.81 s | 152.97 s | 152.92 s | 152.98 s | 152.55 s | 152.78 s |
| | 172.19 s | 169.95 s | 170.75 s | 170.13 s | 170.98 s | 169.69 s | 170.31 s |
| | 175.15 s | 171.70 s | 172.41 s | 172.37 s | 172.47 s | 171.84 s | 172.10 s |

Figure 3:
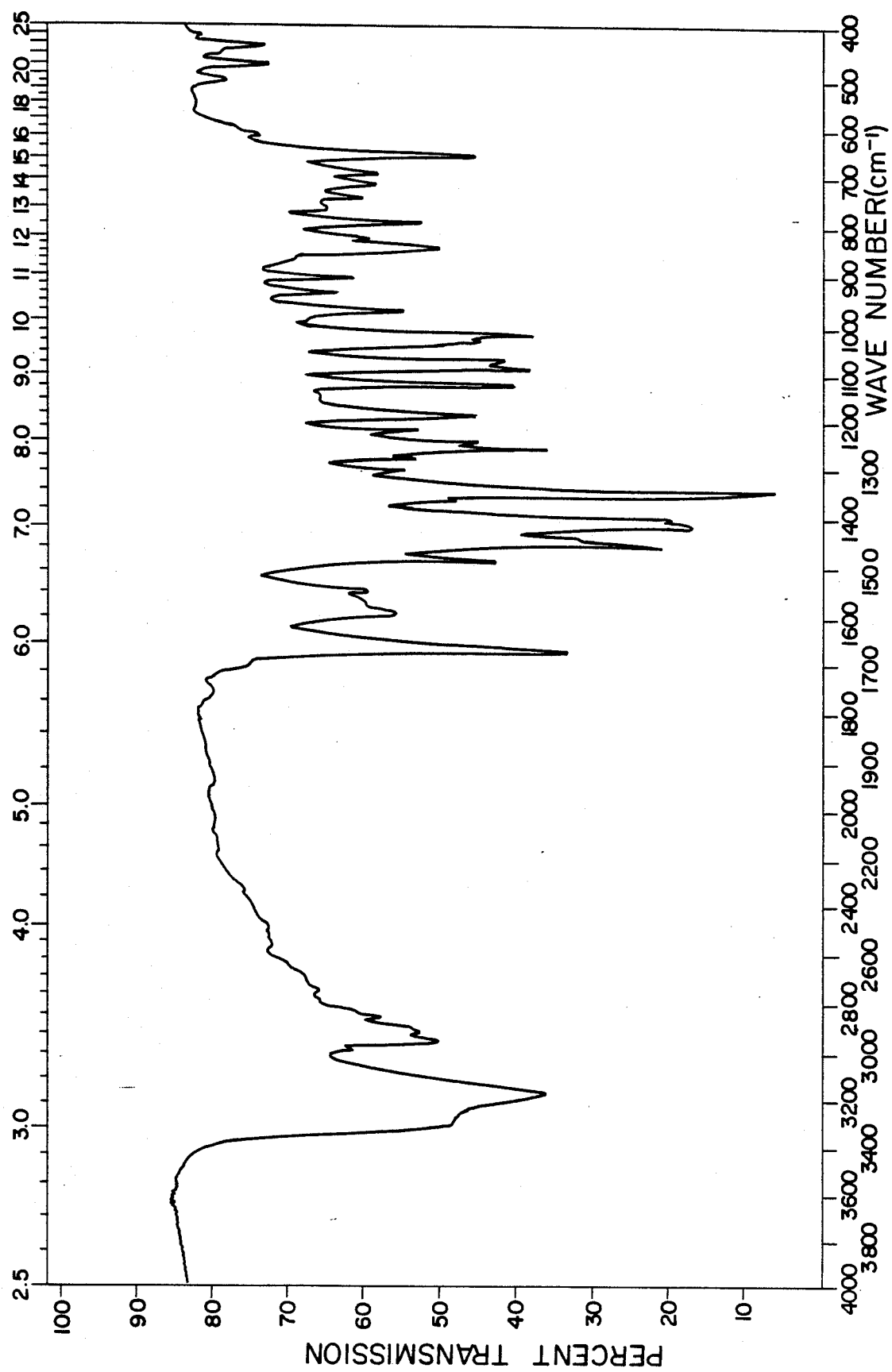
FIG. 3 depicts the infrared spectrum of BU-3557B$_2$, i.e., compound of the above structural formula where R is 4-hydroxypentyl.
Figure 5:
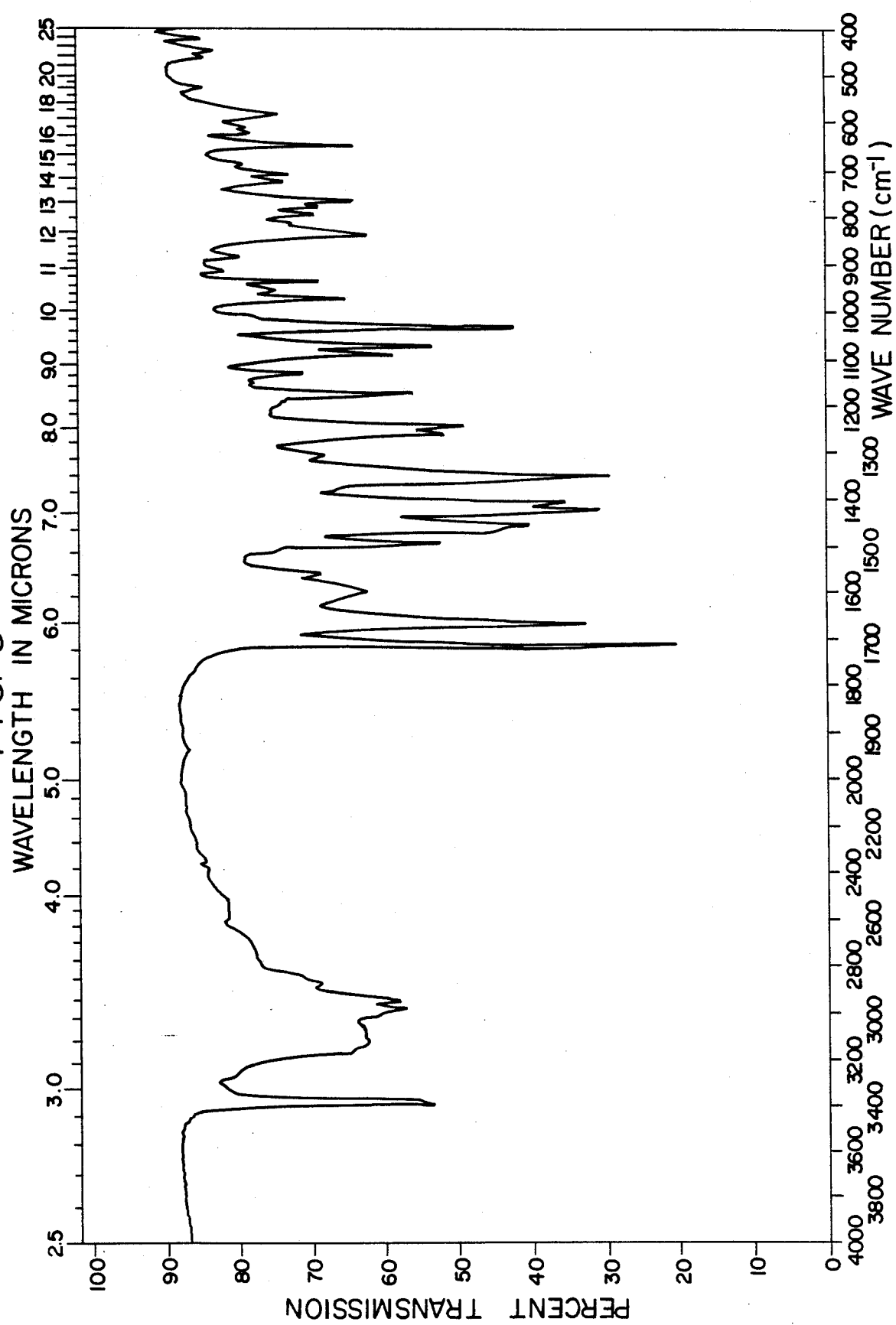
FIG. 5 depicts the infrared spectrum of BU-3557C$_4$, i.e., compound of the above structural formula where R is 3-methyl-4-oxopentyl.
Figure 7:
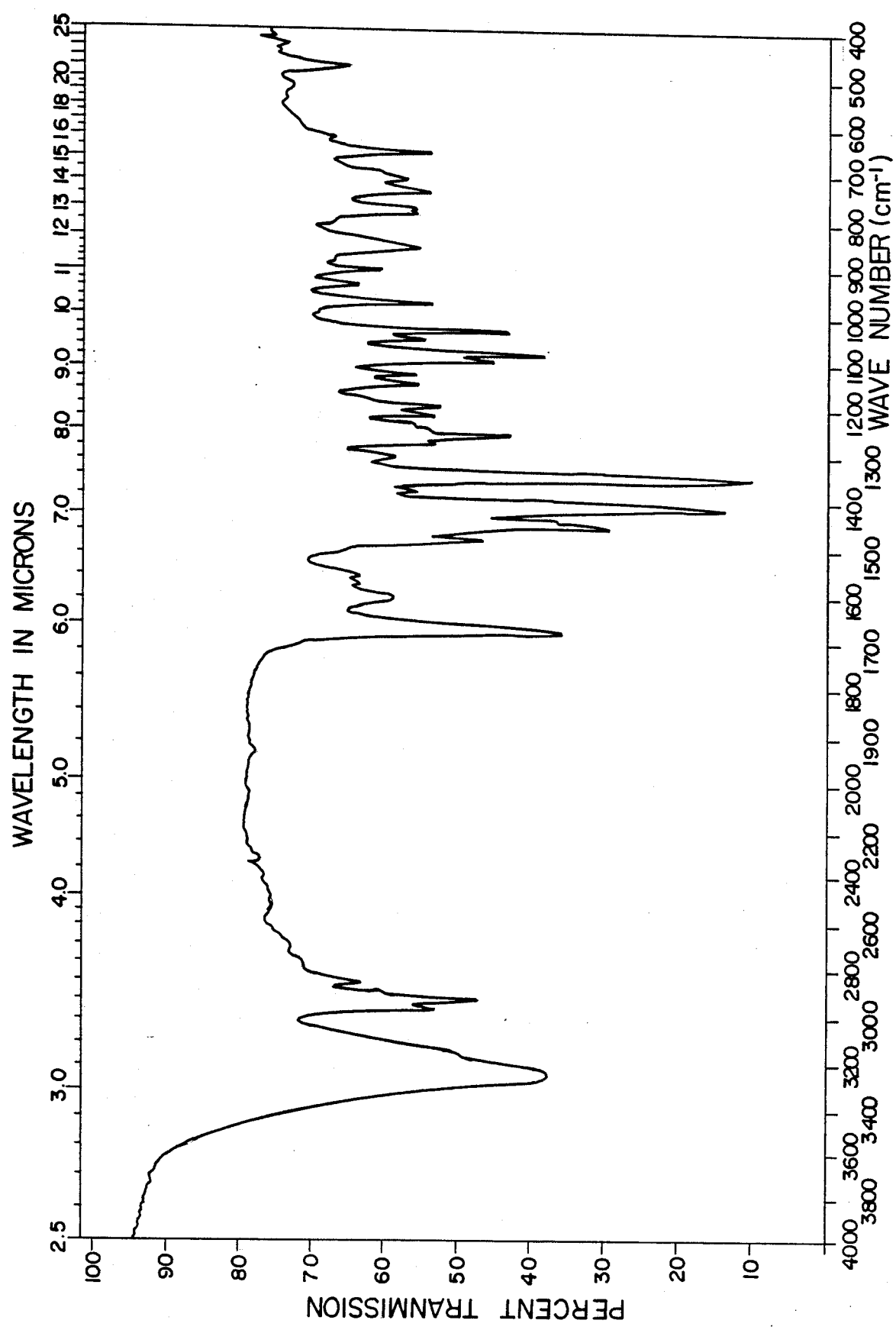
FIG. 7 depicts the infrared spectrum of BU-3557D, i.e., compound of the above structural formula where R is 5-hydroxy-5,5-dimethylpentyl.

The IR spectra for BU-3557A₃, BU-3557B₂, BU-3557C₄ and BU-3557D are respectively presented in FIGS. 1, 3, 5 and 7.

Each of the specific compounds referred to in Table I was soluble in benzene, chloroform, dimethyl sulfoxide, ethyl acetate, methanol and ethanol, but insoluble in n-hexane and water. They gave positive responses to Dragendorff and Rydon-Smith reagents, but negative responses to Erhlich, Sakaguchi and ninhydrin reagents. UV absorption maxima were observed at about 219, 242 and 317 nm in methanol and acidic methanol which shifted to about 221, 252, 293 and 342 nm in alkaline methanolic solution. The IR spectra of these compounds exhibited in common the presence of amide at 1660–1680 cm$^{-1}$. The IR spectra for BU-3557B₁ and BU-3557C₄ showed an additional carbonyl absorption at 1705 cm$^{-1}$ which is attributed to the ketone carbonyl group in the alkyl chain of R.

As indicated, the structure of BU-3557B₂ was elucidated by x-ray crystallography. The spectral data was consistent. The $^1$H-NMR spectrum indicated one C-CH₃ (δ: 1.18, 3H, d), three CH₂ (1.64, 2H, 2.00 and 2.20, 2H and 3.00 and 3.25, 2H), one CH (3.94, 1H two OCH₃ (3.97, 3H and 4.09, 3H) and one aromatic proton (7.90, 1H). The spectrum also contained four other protons (5.62, 6.88, 9.78, and 12.91) which disappeared upon D₂O addition. The $^{13}$C-NMR displayed seven aliphatic carbon signals at δ: 22 ), 23.3 (q), 31.7 (t), 39.0 (t), 60.7 (q), 60.8 (q) and 65.2 . (d) in addition to eight aromatic carbon signals and one carbonyl signal. The $^{13}$C- and $^1$H-NMR studies demonstrated that the other components possessed an identical bis-heteroaromatic nucleus with that of BU-3557B₂, while differing only in the alkyl side chain.

A complex comprising the specifically recited compounds (BU-3557A₁, BU-3557A₂, BU-3557A₃, BU-3557B₁, BU-3557B₂, BU-3557B₃, BU-3557C₁, BU-3557C₂, BU-3557C₃, BU-3557C₄, BU-3557C₅, and BU-3557D) is prepared by fermenting a culture of a newly uncovered strain of Saccharothrix and is readily recovered, e.g., by adsorption utilizing nonionic porous polymer resin absorbent. The individual compounds can be recovered from the complex by chromatography.

The newly uncovered strain of Saccharothrix has been designated *Saccharothrix aerocolonigenes* strain N806-4. This organism was isolated from a soil sample collected in Sankishwar, Karnataka State, India. A biologically pure culture of this organism has been deposited with the American Type Culture Collection, 12301 Parklawn Drive, Rockville, Md., 20852, and added to its permanent collection of microorganisms as ATCC 53712. The permanency of the deposit of this culture and ready accessibility thereto by the public are afforded throughout the effective like of the patent in the event the patent is granted. Access to the culture is available during the pendency of the application under 37 CFR 1.14 and 35 USC 112. All restrictions on the availability to the public of the culture deposited will be irrevocably removed upon granting of the patent.

The morphology, cultural and physiological characteristics, and cell chemistry of strain N806-4 indicate genus Saccharothrix. Based on the further physiological characterization, the strain was identified as *S. aerocolonigenes*. We turn now in detail to the morphology, cultural characteristics, physiologic characteristics, cell chemistry and taxonomic position.

Morphology Strain N806-4 forms branched hyphae which develop into substrate and aerial mycelia. Typical nocardioform fragmentation of substrate mycelium, which affords rod or coccoid elements, is not observed, but partial fragmentation occurs. Lone straight chains of cylindrical segments (0.4–0.6×0.8–1.8 μm) are formed in the total parts of aerial mycelium on tyrosine agar (=ISP medium No. 7) or glucose-asparagine agar. After further incubation, spores are formed discontinuously with intercalary empty hyphae in the segmented aerial mycelium. The mature spores are oval (0.6–0.8×0.8–1.2 μm), non-motile, and have smooth surfaces. The aerial mycelia often fuse into thick fascicle which occurs also in the sporulated hyphae. Constricted zigzag hyphae and sclerotic granule are occasionally observed on the aerial mycelium.

Cultural characteristics: Aerial mycelium is formed moderately on glycerol-asparagine agar (=ISP medium No. 5) and tyrosine agar (=ISP medium No. 7), and very poorly or not formed in ISP media Nos. 2, 3, 4, and 6 and Czapek's sucrose-nitrate agar. The color of the aerial mycelium is white. The color of the substrate mycelium is colorless, orange yellow or light yellowish brown. Melanoid and other diffusible pigments are not formed. The cultural characteristics are presented in Table IV below.

5% but not at 4% or less. It is resistant to lysozyme. The physiological characteristics and carbohydrate utilization are presented in Table V below. The results of additional physiological test (as described by Gordon, R. E. et al, 37 Some bits and pieces of the genus Nocardia: *N. carnea, N. vaccinii, N. transvalensis. N. orientalis* and *N. aerocolonigenes*", J. Gen. Microbiol. 109: 69–78, 1978) are presented in Table VI below.

TABLE V

| Physiological characteristics of strain N806-4 | |
|---|---|
| Hydrolysis of: | |
| Gelatin | + |
| Starch: | |
| Soluble starch | + |
| Potato starch | +(w)* |
| Milk coagulation | + |
| Peptonization | + |
| Production of: | |
| Nitrate reductase | + |
| Tyrosinase | − |
| Tolerance to: | |
| Lysozyme, 0.01% (w/v) | + |
| NaCl, 1~4% (w/v) | + |
| NaCl, 5% (w/v) | − |
| Temperature: | |
| Growth range | 22° C.~42° C. |
| No growth | 18° C. & 45° C. |
| pH: | |
| Growth | 4.5~12.0 |
| No growth | 4.0 & 12.5 |
| Utilization of: | |
| Glycerol | + |
| D(−)-Arabinose | +(w) |
| L(+)-Arabinose | + |
| D-Xylose | + |
| D-Ribose | + |
| L-Rhamnose | +(w) |
| D-Glucose | + |
| D-Galactose | + |
| D-Fructose | + |
| D-Mannose | + |
| L(−)-Sorbose | − |
| Sucrose | + |

TABLE IV

| | Cultural characteristics of strain N806-4 | | |
|---|---|---|---|
| Medium | Growth Aerial mycelium | Substrate mycelium | Diffusible pigment |
| Sucrose nitrate agar (Czapek-Dox agar) | Moderate Scant; white | Moderate orange yellow (71) | Pale yellow (89) |
| Tryptone-yeast extract broth (ISP No. 1) | Moderate, floccose and not turbid | | None |
| Yeast extract-malt extract agar (ISP No. 2) | Good Poor; white | Dark orange yellow (72) | None |
| Oat meal agar (ISP No. 3) | Moderate Poor; white | Moderate yellow (87) to colorless | None |
| Inorganic salts-starch agar (ISP No. 4) | Moderate Poor; white | Moderate orange yellow (71) to light orange yellow (70) | None |
| Glycerol-asparagine agar (ISP No. 5) | Moderate Moderate; white | Pale yellow (89) | None |
| Peptone-yeast extract-iron agar (ISP No. 6) | Moderate Scant; white | Colorless | None |
| Tyrosine agar (ISP No. 7) | Moderate Moderate; white | Moderate olive brown (95) | Grayish yellow (90) |
| Glucose-asparagine agar | Moderate Poor; white | Pale yellow (89) | None |
| Nutrient agar | Poor None | Colorless | None |
| Bennett's agar | Moderate Poor; white | Dark orange yellow (72) | None |
| Papavizas' V-8 juice-dextrose-yeast extract agar | Moderate Poor; white | Strong yellowish brown (74) | None |

Observation after incubation at 28° C. for 3 weeks.
Color and number in parenthesis follow ISOC-NBC designation.

Physiological characteristics' The growth temperature ranges from 22° C. to 42° C. No growth occurs at 18° C. and 45° C. The growth is restricted by NaCl at

| Lactose | + |

TABLE V-continued

| Physiological characteristics of strain N806-4 | |
|---|---|
| Cellobiose | + |
| Melibiose | + |
| Trehalose | + |
| Raffinose | +(w) |
| D(+)-Melezitose | − |
| Soluble starch | + |
| Cellulose | − |
| Dulcitol | − |
| Inositol | + |
| D-Mannitol | + |
| D-Sorbitol | − |
| Salicin | + |

*+(w): weakly positive

TABLE VI

| Additional physiological characteristics of strain N806-4 | |
|---|---|
| Hydrolysis of: | |
| Adenine | − |
| Hypoxanthine | + |
| Tyrosine | + |
| Xanthine | − |
| Casein | + |
| Urea | + |
| Esculin | + |
| Hippuric acid | + |
| Survival at 50° C., 8 hr | − |
| Utilization of: | |
| Benzoate | − |
| Citrate | + |
| Mucate | − |
| Succinate | + |
| Tartrate | − |
| Acid formation: | |
| Glycerol | + |
| D(−)-Arabinose | + |
| L(+)-Arabinose | + |
| D-Xylose | + |
| L-Rhamnose | + |
| D-Glucose | + |
| D-Mannose | + |
| Lactose | + |
| Cellobiose | + |
| Melibiose | + |
| Trehalose | + |
| Raffinose | + |
| D(+)-Melezitose | − |
| Inositol | + |
| D-Mannitol | + |
| D-Sorbitol | − |
| Erythritol | − |
| Methyl α-glucoside | − |
| Adonitol | − |

Cell chemistry: The presence of meso-diaminopimelic acid, ribose, glucose, galactose and mannose in the whole cell hydrolysate of strain N806-4 indicates that the strain belongs to the cell wall type III and sugar pattern C. The strain has the type PII phospholipid (presence of phosphatidylethanolamine and phosphatidylinositol), and contains MK-9($H_4$) as the major menaquinone. Glycolate test is negative. Mycolic acid is absent.

Taxonomic position: The morphology, cultural characteristics and cell chemistry of strain N806-4 place it in the genus Saccharothrix, (Labeda, D. P. et al, "Saccharothrix: a new genus of the Actinomvcetales related to Nocardiopsis, "Int. J. Syst. Bacteriol 34' 426–431, 1984) in which two species, S. australiensis (See Labeda, D. P. et al infra.) and S. aerocolonigenes (Labeda, D., Int. J. System. Bacteriol. 36: 109–110, 1986, and Shinobu, R., et al, Bot. Mag, Tokyo, 73: 212–216, 1960) have been described. S. australiensis is different from strain N806-4 in the following characteristics: the formation of light brownish gray aerial mycelium and dark brown vegetative mycelium in ISP medium No. 2, and clear difference in Gordon's physiological tests. Among the known strains of S. aerocolonigenes. only strain C38383 (ATCC 39243) which is a rebeccamycin-producing organism, forms spore chains on the aerial mycelium. Morphologically, strain N806-4 is related to strain C38383. In addition, strain N806-4 is well consistent with strain C38383 and other strains of S. aerocolonigenes in the physiological characteristics of Gordon's tests. Thus strain N806-4 was classified as Saccharothrix aerocolonigenes.

The fermentation of a culture of the newly uncovered strain of Saccharothrix which has been designated Saccharothrix aerocolonigenes strain N806-4 (ATCC 53712) or variant or mutant thereof to produce the aforedescribed antifungal antibiotic complex (comprising BU-3557$A_1$, BU-3557$A_2$, BU-3557$A_3$, BU-3557$B_1$, BU-3557$B_2$, BU-3557$B_3$, BU-3557$C_1$, BU-3557$C_2$, BU-3557$C_3$, BU-3557$C_4$, BU-3557$C_5$ and BU-3557D), which is sometimes referred to hereafter as BU-3557 complex, is carried out under aerobic conditions in an aqueous nutrient medium containing assimilable sources of carbon and nitrogen until a substantial amount of said complex is produced, i.e., an amount suitable for recovery. In the production of novel antifungal antibiotic compound here, BU-3557 complex is recovered from the fermentation medium and individual compounds are separated from the complex, e.g., by chromatography. Other compounds within the genus herein are prepared from said individual compounds, if desired, by methods known for substituting on alkyl substituent at the 2-position of thiazolyl moiety or rearranging substituents thereon, with appropriate blocking groups being utilized if necessary.

A biologically pure culture of the microorganism Saccharothrix aerocolonigenes strain N806-4 (ATCC 53712) which is capable of producing said complex in a recoverable quantity upon aerobic cultivation is an aqueous nutrient medium containing assimilable sources of carbon and nitrogen is novel and constitutes one aspect of the invention herein.

Turning now to the aforedescribed fermentation, the aqueous nutrient medium consists essentially of assimilable sources of carbon and nitrogen and sterile water. Calcium source (very preferably calcium carbonate) is preferably present. Sodium chloride can also be included. Typically, carbon source is present in an amount by weight of from about 0.5% to about 5%, and nitrogen source is present in an amount by weight of about 0.2% to about 5%. Calcium source is preferably present in an amount by weight ranging from 0.05% to about 1%. Sodium chloride can be included, for example, in an amount of about 0.1% to about 0.3% by weight.

Suitable carbon sources include, for example, arabinose, xylose, ribose, glucose, fructose, sucrose, lactose, soluble starch, mashed potatoes, glycerol, mannitol, sorbitol, etc.

Suitable nitrogen sources include, for example, casein, NZ-case, soybean meal, soy flour, soybean powder, cottonseed meal, cottonseed flour, peanut meal, wheat gluten, meat meal, meat, fish meal, fish extract, yeast extract, peptone, corn steep liquor, etc.

The fermentation is effected at any temperature conducive to satisfactory growth of the producing organism, i.e., 22° C. to 42° C. and is conveniently carried out at a temperature of about 27° C. to 32° C. Preferably, the fermentation is carried out under submerged aerobic conditions with agitation.

In carrying out said fermentation, preferably a see culture obtained by growing from a slant is used to inoculate either shake flasks or inoculum tanks. The seed culture is readily produced by shake cultivation for from 3 to 5 days. Cultivation in the shake flasks or inoculum tanks is preferably carried out until assay indicates peak antibiotic (antifungal potency determined, for example, using an indicator organism (e.g., *Candida alibcans* A9540) or HPLC.

A shake flask is usually run at 100 to 300 rpm and normally reaches maximum growth in 5 to 7 days. An inoculum tank may be agitated at 100 to 300 rpm and is preferably employed with aeration rate of $\frac{1}{2}$ to 2 volumes of sterile free air per volume of fermentation broth per minute forced into the broth through a sparger and under these conditions peak antibiotic potency is normally obtained in 3 to 5 days.

The produced antibiotic complex is readily recovered by harvesting the resulting fermentation broth, separating the broth to cake and supernatant, e.g., utilizing a centrifuge, and recovering the antibiotic complex from the supernatant, for example, by absorbing it utilizing nonionic porous (macroreticular) polymer resin, e.g., Diaion HP-20 from Mitsubishi Kasei, and eluting the complex therefrom and concentrating in a plurality of stages to recover a crude solid comprising the antibiotic complex which is separated into individual antibiotic components within the scope of the invention by chromatography.

As indicated hereinbefore the compounds of the instant invention are useful for controlling fungal infections and are preferably administered in the form of a pharmaceutical composition comprising an effective antifungal amount of compound of the instant invention in combination with a pharmaceutically acceptable carrier or diluent.

Antifungal compositions herein may be made up in any suitable form appropriate for desired use, e.g., oral, parenteral or topical administration. Examples of parenteral administration are intramuscular intravenous, intraperitoneal, rectal and subcutaneous administration.

The diluent or carrier ingredients should not be such as to diminish the therapeutic effects of the antifungal antibiotic.

Suitable dosage forms for oral use include tablets, dispersible powders, granules, capsules, suspensions, syrups, and elixers. Inert diluents and carriers for tablets include, for example, calcium carbonate, sodium carbonate, lactose and talc. Tablets may also contain granulating and disintegrating agents such as starch and alginic acid, binding agents such as starch, gelatin and acacia, and lubricating agents such as magnesium stearate, stearic acid and talc. Tablets may be uncoated or may be coated by known techniques, e.g., to delay disintegration and absorption. Inert diluents and carriers which may be used in capsules include, for example, calcium carbonate, calcium phosphate and koalin. Suspensions, syrups and elixers may contain conventional excipients, for example, methyl cellulose, tragacanth, sodium alginate; wetting agents, such as lecithin and polyoxyethylene stearate; and preservatives, e.g., ethyl-p-hydroxybenzoate.

Turning now to dosage forms suitable for parenteral administration, these include solutions, suspensions, dispersions, emulsions and the like. They may also be manufactured in the form of sterile solid compositions which can be dissolved or suspended in sterile injectable medium immediately before use. They may contain suspending or dispersing agents known in the art.

For topical application, pharmaceutical compositions containing compound within the scope of the present invention in combination with a pharmaceutical carrier or diluent may be in the form, for example, of solutions, pastes, creams, ointments, gels and waxes. Suitable carrier and diluent ingredients include, for example, zinc oxide paste, sorbitol solution, water, starch, mineral oil, white petrolatum, waxes (e.g., paraffin), fatty alcohols (e.g. cetyl alcohol) and fatty acid esters (e.g., containing 12 to 18 carbon atoms in the fatty acid moiety and 1 to 3 carbon atoms in the ester moiety, such as isopropyl laurate, isopropyl myristate, isopropyl palmitate, methyl stearate or ethyl stearate) and fatty oils.

One aspect of the invention herein is directed to therapeutically treating on animal host affected by a fungal infection sensitive to compound of the instant invention which comprises administering to said host an effective antifungal dose of said compound. It will be appreciated that the actual preferred amount of compound of the instant invention used will vary according to the particular compound, the particular composition formulated, the mode of application and the particular situs, host and disease being treated. Many factors that modify the action will be taken into account by those skilled in the art, e.g., age, body weight, sex, diet, time of administration, route of administration, rate of excretion, condition of the host, drug combinations, reaction sensitivities and severities and severity of disease. Administration can be carried out continuously or periodically within the maximum tolerated dose. Optimal application rates for a given set of conditions can be ascertained by those skilled in the art using conventional dosage administration tests in view of the above guidelines.

Compounds within the present invention have exhibited significant in vitro antifungal activity against *Candida alibcans. Aspergillus fumiqatus* and *Trichophvton mentagrophvtes* by the serial broth dilution method and moderate in vitro antifungal activity against *Candida albicans, Cryptococcus neoformans. Aspergillus fumigatus. Piricularia oryzae. Trichophyton mentagrophytes, Blastomyces dermititidis. Sporothrix schenckii* and *Mucor spinosus.* Furthermore, in vivo antifungal activity against *C. albicans* systemic infection has been indicated at doses of 3.1 to 25 mg/kg, preferably 6.3 to 12.5 mg/kg for compounds of the invention where R is 1,5-dihydroxy-5,5-dimethylpentyl (BU-3557A$_3$) when administered intramuscularly twice a day for two days. Furthermore, in vivo antifungal activity against *Candida albicans* vaginal infection has been demonstrated for BU-3557B$_2$ when administered topically for 5 days at an EC$_{50}$ (concentration for 50% inhibition compared to a control) of 0.34%.

In vitro antibacterial activity has also been demonstrated against Gram-positive bacteria for compounds of the invention herein.

Furthermore BU-3557B$_2$ has demonstrated in vitro antiprotazoal (anti-trichomonal) activity against a clinical isolate of *trichomonas vaginalis.*

The following examples are provided for illustrative purposes only and are not intended to limit the scope of the invention.

EXAMPLE I

Production of Antifungal Complex BU-3557 By Flask Fermentation

A loopful of the slant culture of *Saccharothrix aerocolonigenes* strain N806-4 (ATCC 53712) was inoculated in a 500-ml Erlenmeyer flask containing 100 ml of the following seed medium' soluble starch 0.5%, glucose 0.5%, fish extract (Mikuni) 0.1%, yeast extract (Oriental) 0.1% NZ-case (Sheffield) 0.2% and $CaCO_3$ 0.1%. Shake cultivation was carried out at 28° C. for 4 days on a rotary shaker (200 rpm). The seed culture (2 ml) was inoculated into a 500-ml Erlenmeyer flask which contained 100 ml of the fermentation medium composed of mashed potato (Snow Milk Products) 4% corn steep liquor 2%, NaCl 0.2% and $CaCO_3$ 0.3%; being adjusted to pH of 7.2 before being autoclaved. The fermentation was carried out on a rotary shaker (200 rpm) at 28° C. for 8 days. For the assay of antifungal activity, the broth dilution method was used with a 96-well microtitre plate using *Candida alibcans* A9540 as the indicator organism. The activity was determined by Titertek Multiskan MCC (Flow Laboratories) at 540 nm. HLPC was also used for determining BU-3557 complex. The antifungal activity of the flask fermentation reached maximum on the 6th day.

EXAMPLE II

Production of Antifungal Complex BU-3557 By Tank Fermentation and Separation of Complex into Components (1) Fermentation to produce BU-3557 complex Tank fermentation was carried out. The seed culture was prepared by the same procedure as in Example I using the following seed medium: glucose 2%, soybean meal 1% and $CaCO_3$ 0.5%. After shaking cultivation on a rotary shaker at 28° C. for 4 days, the seed culture (2 liters) was inoculated to 200-liter fermentation tank (Marubishi MPF-U200) which contained 120 liters of the fermentation medium having the same composition as for the flask fermentation in Example I. The tank fermentor was operated at 28° C. with agitation at 250 rpm and aeration rate of 120 liters/min. The broth pH gradually rose with the progress of fermentation and reached 7.7 to 7.8 after 90 hrs when a peak antibiotic potency of 112 μg/ml (HPLC assay) was obtained.

(2) Isolation and purification of components of BU-3557 complex (a) Extraction and primary separation The harvested fermentation broth (265L) was separated to supernatant and mycelial cake by use of a Sharpless A centrifuge (Kokusan No. 4A). The clear supernatant (232 L) was stirred wit Diaion HP-20 (23 L) for 1.5 hours. (Diaion HP-20 is a trademark of Mitsubishi Chemical Industries of Japan for a nonionic macroreticular, i.e., macroporous, polymer resin). The resin was collected by filtration, washed twice with 50% aqueous methanol (22 L each) and eluted three times with 23 L each of 80% aqueous acetone. The eluates were combined and concentrated in vacuo and the aqueous concentrate (17 L) was charged on a column of Diaion HP-20 (3.4 L). The column was washed with 50% aqueous methanol (10 L) and developed with 60% aqueous acetone. The eluate was collected in fractions which were examined by paper-disc assay using *Cryptococcus neoformans* IAM-4514 (Cn-2). The active fractions were pooled, concentrated in vacuo and extracted twice with 3.5 L each of ethyl acetate. Evaporation of the extract in vacuo yielded a crude solid of BU-3557 complex (18.5 g).

Crude solid (2.4g) was applied on a column of LiChroprep RP-18 (Merck, 22×450 mm) which had been equilibrated by a mixture of acetonitrile and 0.15% $KH_2PO_4$ (36:64 v/v, pH 3.5 by an addition of $H_3PO_4$). Elution was carried out with the same solvent mixture using an FMI A medium pressure LAB pump (Fluid Metering Inc.), and the eluate was monitored by Cn-2 and HPLC. BU-3557A complex was eluted first followed by BU-3557$B_2$, then a mixture of BU-3557$B_1$, $B_2$ and $B_3$ complex and finally BU-3557C and D complex. Each fraction was concentrated in vacuo to remove the acetonitrile and extracted with ethyl acetate. The extract was concentrated in vacuo to give the four fractions of BU-3557. Repetition of this chromatography seven times starting from 2.4 g each of crude solid yielded BU-3557A complex (2.4g), semi-pure BU-3557 $B_2$ (3.4g), BU-3557$B_1$, $B_2$ and $B_3$ complex (2.0g) and BU-3557C and D complex (1.3 g).

(b) Purification of BU-3557A complex

The BU-3557A complex obtained above was a mixture of three sub-components (BU-3557$A_1$, $A_2$, $A_3$) by HPLC analysis. The complex solid (2.3 g) was chromatographed on a column of LiChroprep RP-18 (22×450 mm) eluting with acetonitrile-0.15% $KH_2PO_4$, pH 3.5 (33.3: 66.7 v/v) mixture. Upon monitoring the eluate by HPLC, BU-3557$A_1$, and $A_2$ complex was eluted first followed by nearly only BU-3557$A_3$. The relevant fractions were concentrated and each concentrate was extracted with ethyl acetate. Evaporation of the extracts gave semi-pure BU-3557$A_1$ and $A_2$ complex (601 mg) and semi-pure BU-3557$A_3$ (984 mg).

The BU-3557$A_1$ and $A_2$ complex (550 mg) was rechromatographed on a column of YMC GEL ODS A60 (Yamamura Chemical Co., 22×450 mm). Elution was carried out with a mixture of methanol-0.03 M phosphate buffer pH 7.0 (48:52, v/v) and the bioactive eluates were examined by HPLC. The first active fractions containing homogeneous BU-3557$A_1$ were pooled, concentrated and then extracted with ethyl acetate. Evaporation of the extract yielded a white solid of pure BU-3557$A_1$ (41 mg). The second active fractions were similarly worked up to give pure BU-3557$A_2$ (18 mg).

The semi-pure sample of BU-3557$A_3$ (705 mg) was purified by a column of YMC GEL ODS A60 (22×450 mm) developed with a mixture of methanol-0.03M phosphate buffer pH 7.0 (50:50, v/v). Upon examination of the eluates by HPLC, the heart-cuts of BU-3557$A_3$ fractions were concentrated in vacuo to remove the methanol. Extraction of the concentrate with ethyl acetate followed by concentration of the extract afforded pure BU-3557$A_3$ (123 mg).

(c) Purification of BU-3557B fraction

The BU-3557$B_2$ main fraction (568 mg) was purified by a preparative HPLC using a Gilson Model 303 system with a semi-preparative SSC-ODS-842 column (Senshu Kagaku Co. 30×250 mm). The elution solvent was a mixture of methanol-0.03M phosphate buffer pH 7.0 (Time 0-15 min. 54/46, 15-80 min.: linear gradient of 54/46-65/35 and 80-100 min.: 65/35 v/v, flow rate 12.0 ml/min) and eluates were monitored by UV absorption at 280 nm. BU-3557$B_1$ was eluted at the retention time of 47 min. followed by BU-3557$B_2$ at 58 min. and then BU-3557$B_3$ at 72 min. The appropriate eluates were pooled and concentrated to remove the methanol.

The aqueous concentrate of BU-3557B$_1$ fractions were passed through a column of Diaion HP-20 (20×300 mm). The column was washed with 50% aqueous methanol (200 ml) and then eluated with 80% aqueous acetone (100 ml). Evaporation of the acetone eluate yielded homogeneous BU-3557B$_1$ (22.3 mg). The concentrates of BU-3557B$_2$ and B$_3$ fractions were similarly treated to give pure solids of BU-3557B$_2$ (229.6 mg) and BU-3557B$_3$ (15.4 mg) respectively. The crude solid of BU-3557 B$_1$, B$_2$, B$_3$ complex (750 mg) was purified by the preparative HPLC as described above to yield pure BU-3557B$_1$ (54.4 mg), B$_2$ (55.3 mg) and B$_3$ (203.9 mg).

(d) Purification of BU-3557C and D complex

Separation of BU-3557C and D complex (1.21 g) was achieved by a medium pressure liquid chromotography with a LiChroprep RP-18 column (22×450 mm). The elution was performed first with a mixture of methanol-0.03M phosphate buffer pH 7.0 (52/48 v/v, 1.0 L and then a linear gradient of the mixture 52/48 to 60/40, a total volume 1.OL). Fractionation of the eluate was guided by HPLC and the two active fractions were worked up to yield BU-3557C complex (545 mg) and pure BU-3557D (379 mg).

BU-3557C complex contained five sub-components, BU-3557C$_1$, C$_2$, C$_3$, C$_4$, C$_5$ by HPLC analysis. The complex (66 mg) was charged on a semi-preparative SSC-ODS-842 column (30×250 mm). Elution was carried out with a mixture of acetonitrile and 0.15% KH pH 3.5 (Time 0–15 min.: 25/75–41.5/58.5, 15–70 min: 41.5/58.5, 70–90 min.: 41.5/58.5–55/45). Upon monitoring by UV absorption at 300 nm, the relevant fractions (C$_1$: Rt 57.2, C$_2$ 58.5, C$_3$: 63.2, C$_4$:70.2 and C$_5$: 80.7) were pooled. This semi-preparative HPLC was repeated 7 times and the appropriate fractions were combined. Each fraction was concentrated and extracted twice with ethyl acetate. Evaporation of the extracts gave pure BU-3557C$_1$ (22.8 mg), BU-3557C$_2$ (23.6 mg), BU-3557C$_3$ (110.0 mg), BU-3557C$_4$ (75.0 mg) and BU-3557C$_5$ (33.0 mg).

EXAMPLE III

BU-3557 complex is prepared in a similar manner so that prepared in Example I.

HPLC of the components of said complex is shown in Table VII below.

TABLE VII

| Component | Retention time |
| --- | --- |
| BU-3557 A$_1$ | 7.14 |
| BU-3557 A$_2$ | 7.46 |
| BU-3557 A$_3$ | 7.89 |
| BU-3557 B$_1$ | 9.44 |
| BU-3557 B$_2$ | 8.87 |
| BU-3557 B$_3$ | 9.57 |
| BU-3557 C$_1$ | 10.34 |
| BU-3557 C$_2$ | 10.63 |
| BU-3557 C$_3$ | 10.99 |
| BU-3557 C$_4$ | 11.53 |
| BU-3557 C$_5$ | 12.48 |
| BU-3557 D | 11.72 |

Condition
column: Microsorb Short One C$_{18}$ (4.6 mm I.D. × 100 mm, 3 μm)
mobile phase: Solvent A: 0.15% KH$_2$PO$_4$ adjusted to pH 3.5 with H$_3$PO$_4$
Solvent B: CH$_3$CN

| Time (min.) | 0–3 | 3–9 | 9–14 |
| --- | --- | --- | --- |
| A/B | 85/15–60/40 | 60/40 | 60/40–45/55 | flow rate: 1.2 ml/min
detection: UV absorption at 254 nm

EXAMPLE IV

In Vitro Antifungal Activity

The in vitro antifungal activity of the components of BU-3557 was determined against various fungi by serial broth (results in Table VIII below) and agar (results in Table IX below) dilution methods. Sabouraud dextrose broth and agar were used for these experiments. The inoculum size was adjusted to $10^4$–$10^6$ and $10^5$–$10^9$ CFU/ml for both methods. After incubation at 28° C. for 48 or 72 hours, the minimum inhibitory concentration (MIC), the lowest concentration of antibiotic causing virtually complete inhibition of growth, was examined. As shown in Table VIII, all components of BU-3557 exhibited significant in vitro antifungal activity against *Candida albicans*. *Aspergillus fumigatus* and *Trichophyton mentagrophytes* in the broth dilution method. As shown in Table IX, all components of BU-3557 exhibited moderate antifungal activity against various clinically important pathogenic fungi in Sabouraud dextrose agar.

TABLE VIII

In vitro antifungal activity in Sabouraud dextrose broth

MIC (μg/ml)[1]
BU-3557

| Test organism[2] | A1 | A2 | A3 | B1 | B2 | B3 | C1 | C2 | C3 | C4 | C5 | D |
| --- | --- | --- | --- | --- | --- | --- | --- | --- | --- | --- | --- | --- |
| *Candida albicans* A9540 | 50 (1.6)[3] | >100 (3.1) | >100 (3.1) | 12.5 | 3.1 | 6.3 | 3.1 (1.6) | 3.1 (1.6) | 6.3 (3.1) | 6.3 (3.1) | 6.3 (3.1) | 3.1 |
| *Aspergillus fumigatis* IAM 2034 | 6.3 (3.1) | 12.5 (6.3) | 6.3 (3.1) | 6.3 | 6.3 | 12.5 | 3.1 | 3.1 | 3.1 | 3.1 | 3.1 | 3.1 |
| *Trichophyton mentagrophytes* #4329 | >100 (25) | >100 (50) | >100 (50) | 6.3 | 6.3 | 6.3 | 6.3 (3.1) | 6.3 (3.1) | 6.3 (3.1) | 6.3 (3.1) | 6.3 | 6.3 (3.1) |

[1]Determined after incubation for 48–72 hours at 28° C.
[2]Inoculum size: $10^4$–$10^6$ CFU/ml
[3]Values in parenthesis indicate partial inhibition

TABLE IX

In vitro antifungal activity in Sabouraud dextrose agar

MIC (μg/ml)[1]
BU-3557

| Test organism[2] | A1 | A2 | A3 | B1 | B2 | B3 | C1 | C2 | C3 | C4 | C5 | D |
| --- | --- | --- | --- | --- | --- | --- | --- | --- | --- | --- | --- | --- |
| *Candida albicans* IAM 4888 | 25 (12.5)[3] | 100 (12.5) | >100 (<6.3) | 50 | 25 | 50 | 50 (12.5) | 50 (<6.3) | 50 (<6.3) | 50 (12.5) | 50 (12.5) | 50 (12.5) |
| *Candida albicans* A 9540 | 25 (12.5) | >100 (12.5) | >100 (<6.3) | 25 | 25 | 50 | 50 (<6.3) | 50 (<6.3) | 50 (<6.3) | 50 (12.5) | 50 (<6.3) | 50 (12.5) |

TABLE IX-continued

In vitro antifungal activity in Sabouraud dextrose agar

MIC (μg/ml)[1]
BU-3557

| Test organism[2] | A1 | A2 | A3 | B1 | B2 | B3 | C1 | C2 | C3 | C4 | C5 | D |
|---|---|---|---|---|---|---|---|---|---|---|---|---|
| *Cryptococcus neoformans* D 49 | 25 | >100 | >100 | 50 | 25 | 50 | 50 | 50 | 50 | 50 | 50 | 50 |
| *Cryptococcus neoformans* IAM 4514 | 25 | >100 | >100 | 25 | 25 | 50 | 50 | 50 | 50 | 50 | 50 | 50 |
| *Aspergillus fumigatus* IAM 2530 | 25 | 25 | 25 | 50 | 25 | 50 | 25 | 25 | 25 | 25 | 25 | 25 |
| *Aspergillus fumigatus* IAM 2034 | 25 | 25 | 25 | 50 | 25 | 50 | 25 | 25 | 25 | 25 | 25 | 25 |
| *Piricularia oryzae* D 91 | 50 | 50 | 25 | NT[4] | NT | NT | 25 | 25 | 25 | 25 | 25 | 25 |
| *Trichophyton mentagrophytes* D155 | 100 | 50 | 50 | NT | 25 | NT | 25 | 25 | 25 | 25 | 25 | 25 |
| *Trichophyton mentagrophytes* #4329 | 100 | 50 | 50 | 50 | 25 | 50 | 25 | 12.5 | 25 | 25 | 25 | 25 |
| *Blastomyces dermatitidis* D 40 | NT | 25 | 25 | 12.5 | 25 | 25 | 12.5 | 12.5 | 12.5 | 25 | 12.5 | 25 |
| *Sporothrix schenckii* IFO 8158 | 12.5 | >100 | >100 | 50 | 50 | 50 | 25 | 25 | 25 | 25 | 25 | 25 |
| *Mucor spinosus* IFO 5317 | 6.3 | 12.5 | 12.5 | 25 | 12.5 | 25 | <6.3 | <6.3 | <6.3 | 12.5 | <6.3 | <6.3 |

[1]Determined after incubation for 72 hours at 28° C.
[2]Inoculum size: $10^5$–$10^9$ CFU/ml
[3]Values in parenthesis indicate partial inhibition
[4]Not tested

EXAMPLE V

In vivo Antifungal Activity of BU-3557A$_3$ Against *C. albicans* Systemic Infection Testing for In vivo therapeutic efficacy of BU-3557A$_3$ (60% pure material) against *C. albicans* A9540 intravenous infection was carried out. The test organism was cultured for 18 hours at 28° C. in YGP medium (yeast extract, glucose, peptone, K$_2$HPO$_4$, MgSO$_4$) and suspended in saline. Male ICR mice weighing 20 to 24 g were infected intravenously with about 10 time the median lethal dose of the fungi. BU-3557A$_3$ was administered to groups of 5 mice intramuscularly twice a day on days 0 and 1. The results are set forth in Table X below. The dose that protects 50% of the animals from the infection m(PD$_{50}$, mg/kg) was calculated from survival rates examined on the 20th day after infection. BU-3557A$_3$ demonstrated good in vivo efficacy, though the highest dose at 25 mg/kg showed weak toxic sign.

TABLE X

In vivo antifungal activity against *Candida albicans* A 9540 intravenous infection in mice

| Compound | Dose (mg/kg, im/inj.)[1] | Number of survivors/tested |
|---|---|---|
| Bu-3557 A3 (purity 60%) | 25 | 1/5 |
| | 12.5 | 3/5 |
| | 6.3 | 3/5 |
| | 3.1 | 1/5 |

PD$_{50}$ (mg/kg, im/inj.): 5.4
[1]Compound was administered intramuscularly twice a day on days 0 and 1.

EXAMPLE VI

In Vivo Antifungal Activity of BU-3557B$_2$ Against *C. albicans* Vaginal Infection Topical application of BU-3557B$_2$ against *C. albicans* A9540 vaginal infection was examined. Groups of 5 female mice (ICR, 18–21 g) were treated subcutaneously with 0.5 estradiol benzoate 3 days before and 4 days after *C. albicans* A9540 vaginal infection, respectively. A 0.01 ml of the cell suspension of *C. albicans* containing 10$^8$ CFU/ml was inoculated intravaginally on day 0. Then 0.02 ml of the compound solution in Solbase (1'1 mixture of polyethyleneglycol 400 and polyethyleneglycol 4000, Dainippon-Seiyaku) was instilled intravaginally once a day on days 0 to 4. On the day 7, vaginal exudate was taken by a thin glass rod and spread on the YGP agar plate. Viable cell count was made after incubation for 2 days at 28° C. The results are shown in Table XI below. The EC$_{50}$ value, which is the drug concentration (weight %) giving 50% inhibition of the control, was calculated by the method of least squares. As shown in Table XI, BU-3557B$_2$ exhibited potent activity against *C. albicans* vaginal infection by topical application.

TABLE XI

In vivo antifungal activity against *Candida albicans* A 9540 vaginal infection in mice

| Compound | Conc. (%) | No. of cells/plate Mean | % inhibition |
|---|---|---|---|
| Vehicle | — | 284 | |
| BU-3557 B2 | 2.0 | 0 | 100 |
| | 1.0 | 3 | 99 |
| | 0.5 | 10 | 97 |
| | 0.25 | 243 | 14 |
| | 0.13 | 248 | 13 |

EC$_{50}$ (%): 0.34
Compound was applied once a day from day 0 to day 4.

EXAMPLE VII

Testing for In Vitro Antibacterial Activity

The In vitro antibacterial activity of the components of BU-3557 was determined by the serial dilution method in nutrient agar against Gram-positive and Gram-negative aerobic bacteria. The inoculum size was adjusted to 10$^5$–10$^6$ CFU/ml The MIC was defined as the lowest concentration of test compound completely inhibiting bacterial growth after 18 hour-incubation at 37° C. The results are shown in Table XII below. As shown in Table XII, all components of BU-3557 exhibited weak in vitro antibacterial activity against Gram-positive bacteria, but were nearly inactive against Gram-negative organisms.

TABLE XII

In vitro antibacterial activity in nutrient agar

MIC (μg/ml)[1]
BU-3557

| Test organism[1] | A1 | A2 | A3 | B1 | B2 | B3 | C1 | C2 | C3 | C4 | C5 | D |
|---|---|---|---|---|---|---|---|---|---|---|---|---|
| *Staphylococcus aureus* 209 P | 50 | 50 | 50 | 25 | 25 | 50 | 25 | 50 | 100 | 25 | 25 | 50 |
| *Staphylococcus aureus* #52-34[3] | 50 | 100 | 100 | 50 | 50 | 100 | 100 | 100 | >100 | 100 | 100 | 100 |

TABLE XII-continued

| | In vitro antibacterial activity in nutrient agar MIC (μg/ml)[1] BU-3557 | | | | | | | | | | | |
|---|---|---|---|---|---|---|---|---|---|---|---|---|
| Test organism[1] | A1 | A2 | A3 | B1 | B2 | B3 | C1 | C2 | C3 | C4 | C5 | D |
| *Staphylococcus aureus* A 20239[4] | 50 | 100 | 100 | 50 | 50 | 100 | 100 | 100 | >100 | 100 | 50 | 100 |
| *Staphylococcus aureus* BX-1633-2[5] | 50 | 100 | 100 | 50 | 50 | 100 | 100 | 100 | >100 | 100 | 50 | 100 |
| *Staphylococcus aureus* A 15097[6] | 50 | 50 | 50 | 25 | 50 | 50 | 50 | 100 | >100 | 50 | 50 | 50 |
| *Staphylococcus epidermidis* D153 | 50 | 100 | 50 | 50 | 25 | 50 | 25 | 50 | 25 | 50 | 25 | 50 |
| *Enterococcus faecalis* A 9612 | 100 | 100 | 100 | 100 | 100 | >100 | 50 | 100 | >100 | 100 | 50 | 50 |
| *Bacillus subtilis* PCI219 | 50 | 25 | 50 | 25 | 25 | 25 | 25 | 25 | 50 | 25 | 25 | 25 |
| *Escherichia coli* NIHJ | 100 | >100 | >100 | >100 | >100 | >100 | 100 | >100 | >100 | 100 | 100 | 100 |
| *Klebsiella pneumoniae* D 11 | 50 | >100 | >100 | 50 | 50 | 100 | >100 | >100 | >100 | >100 | 100 | >100 |
| *Proteus mirabilis* A 9554 | 100 | >100 | >100 | >100 | >100 | >100 | 100 | >100 | >100 | 100 | 100 | 100 |
| *Proteus vulgaris* A 9436 | 100 | 100 | 100 | >100 | >100 | >100 | 100 | 100 | >100 | 100 | 100 | 100 |
| *Serratia marcescens* A 20222 | >100 | >100 | >100 | >100 | >100 | >100 | >100 | >100 | >100 | >100 | >100 | >100 |
| *Pseudomonas aeruginosa* A 9930 | >100 | >100 | >100 | >100 | >100 | >100 | >100 | >100 | >100 | >100 | >100 | >100 |

[1]Determined after incubation for 18 hours at 37° C.
[2]Inoculum size: $10^5$–$10^6$ CFU/ml
[3]Erythromycin-resistant strain
[4]Kanamycin-resistant strain
[5]Penicillinase-producing strain
[6]Methicillin-resistant strain

EXAMPLE VIII

Testing for In Vitro Anti-trichomonal Activity

BU-3557B$_2$ was tested for in vitro anti-trichomonal activity compared with metronidazole. Table XIII below shows MIC (minimum inhibitory concentration) values determined after 24 hour incubation at 37° C. As indicated in Table XIII BU-3557B$_2$ exhibited appreciable activity against a clinical isolate of *Trichomonas vaginalis*.

TABLE XIII

| In vitro activity against *Trichomonas vaginalis* in thioglycolate broth | | |
|---|---|---|
| | MIC (μg/ml)[1] | |
| Test organism[2] | BU-3557 B2 | Metronidazole |
| *Trichomonas vaginalis* Tv-2 | 25 | 0.8 |

[1]Determined after 24 hour-incubation at 37° C.
[2]Inoculum size: $10^5$ cells/ml Variations will be evident to those skilled in the art. Therefore, the scope of the invention is intended to be defined by the claims.

What is claimed is:

1. The compound having formula

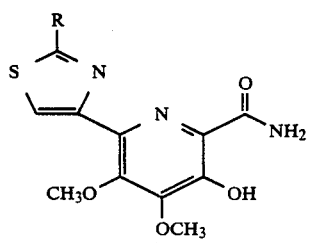

wherein R is selected from the group consisting of
1,4-dihydroxypentyl,
1,4-dihydroxy-4-methylpentyl,
1,5-dihydroxy-5,5-dimethylpentyl,
4-oxopentyl,
4-hydroxypentyl,
4-hydroxy-4-methylpentyl,
3-hydroxypentyl,
4-methyl-5-hydroxypentyl,
3-methyl-4-hydroxypentyl,
3-methyl-4-oxopentyl,
1-hydroxypentyl, and
5-hydroxy-5,5-dimethylpentyl.

2. The compound of claim 1 wherein R is 4-hydroxypentyl.

3. A pharmaceutical composition for treatment of fungal infections comprising an effective antifungal amount of compound as recited in claim 1 in combination with a pharmaceutical carrier or diluent.

4. A pharmaceutical composition as recited in claim 3 wherein said compound is the compound of claim 6.

5. A method for therapeutically treating an animal host affected by a fungal infection sensitive to compound as recited in claim 1 which comprises administering to said host an effective antifungal dose of said-compound.

6. A method as recited in claim 5 wherein said infection is a *Candida albicans* systemic infection and administering of said compound is carried out parenterally.

7. A method as recited in claim 6 wherein said infection is a *Candida albicans* vaginal infection and administering of said compound is carried out by topical application.

8. A method as recited in claim 7 wherein said compound is the compound of claim 6.

* * * * *